United States Patent
Freigang et al.

(10) Patent No.: US 6,730,083 B2
(45) Date of Patent: May 4, 2004

(54) PUNCTURE CANNULA

(75) Inventors: Helmut Freigang, Koerle (DE); Manfred Seeber, Felsberg (DE); Klaus Siemon, Koerle (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 10/143,736

(22) Filed: May 7, 2002

(65) Prior Publication Data

US 2002/0198557 A1 Dec. 26, 2002

(30) Foreign Application Priority Data

May 8, 2001 (DE) .................................. 201 07 778 U

(51) Int. Cl.$^7$ .............................................. A61B 18/18
(52) U.S. Cl. ......................................... 606/41; 606/44
(58) Field of Search ................................ 606/108, 181, 606/41, 44, 43, 185, 189, 32, 34, 36; 604/164.01, 164.06, 164.08, 164.09, 164.1, 164.11, 164.12, 165.01, 170.01, 170.02, 264, 158, 162, 21; 600/554; 439/883, 909, 920, 927, 929; 607/118, 115, 2

(56) References Cited

U.S. PATENT DOCUMENTS

| 839,268 | A | * | 12/1906 | Burch ........................ 606/44 |
| 853,096 | A | * | 5/1907 | Lewis ........................ 606/44 |
| 3,145,261 | A | * | 8/1964 | Forney ...................... 174/84 C |
| 3,249,103 | A | * | 5/1966 | Woodhouse ................. 600/360 |
| 3,605,072 | A | * | 9/1971 | Driscoll ..................... 439/402 |
| 3,682,162 | A | * | 8/1972 | Coyler ....................... 600/373 |
| 4,317,608 | A | * | 3/1982 | Dechelette .................. 439/403 |
| 4,824,433 | A | * | 4/1989 | Marz et al. .................. 604/21 |
| 4,966,588 | A | * | 10/1990 | Rayman et al. ........ 604/165.02 |
| 5,046,506 | A | * | 9/1991 | Singer ........................ 600/554 |
| 5,405,324 | A | * | 4/1995 | Wiegerinck .................. 604/60 |
| 6,440,108 | B1 | * | 8/2002 | Jones ......................... 604/264 |
| 6,456,874 | B1 | * | 9/2002 | Hafer et al. .................. 604/21 |
| 6,491,690 | B1 | * | 12/2002 | Goble et al. .................. 606/41 |
| 6,533,732 | B1 | * | 3/2003 | Urmey ........................ 600/554 |
| 2002/0055761 | A1 | * | 5/2002 | Mann et al. .................. 607/41 |

FOREIGN PATENT DOCUMENTS

EP          0 102 538 B1      3/1984

* cited by examiner

Primary Examiner—Michael J. Milano
Assistant Examiner—D. Jacob Davis
(74) Attorney, Agent, or Firm—Christie, Parker & Hale, LLP

(57) ABSTRACT

A puncture cannula, particularly for nerve stimulation, comprises a steel cannula (10) attached to a cannula hub (11), and a cable (19) extending through an insertion channel (18) and having its core (21) connected to the steel cannula (10). The hub (11) of the cannula (10) comprises a metallic clamping element (24) formed with a first clamping slot engaging the steel cannula (10) and with a second clamping slot engaging the core (21) of the cable (19).

20 Claims, 2 Drawing Sheets

PUNCTURE CANNULA

CROSS-REFERENCE TO RELATED APPLICATION

This application claims priority from German patent Application No. 201 07 778.7, titled PUNCTURE CANNULA, filed in Germany on May 8, 2001, the entire contents of which is incorporated by reference herein as though set forth in full.

FIELD OF THE INVENTION

The instant invention relates to a puncture cannula, particularly for nerve stimulation, comprising a steel cannula attached to a cannula hub and a cable extending through an insertion channel of the cannula hub and having a core connected to the steel cannula.

BACKGROUND OF THE INVENTION

European Patent 0 102 538 B1 discloses a puncturing and catheterizing device which is suited for the puncturing and catheterizing of nerve strings. This device comprises a steel cannula with a cannula hub provided at the distal end of the cannula. The steel cannula is connected to a cable by which an electric potential can be applied to the steel cannula. When the steel cannula, which has an exposed tip, is brought into a position close to a nerve, electrical pulses, which are applied to the cable by a suitable stimulation device, will cause a nerve stimulation, resulting in corresponding reflexes of the patient. In this manner, it can be verified whether the tip of the cannula has been guided sufficiently close to the selected nerve. Thereafter, an anesthetic agent can be injected either through the cannula or through a catheter which has been set by use of the cannula in order to perform local anesthesia. In the known device, the electrical connection of the core of the cable to the steel cannula is performed by winding the core around the cannula, or by soldering the core to the cannula and subsequently enmolding the connection. Such a connection technique is complicated and overly expensive.

It is an object of the invention to provide a puncture cannula which is easily manufactured and guarantees a safe contact between the cable and the puncture cannula.

SUMMARY OF THE INVENTION

According to the instant invention, the hub of the cannula comprises a metallic clamping element which is formed with a first clamping slot for engaging the steel cannula and with a second clamping slot for engaging the core of the cable. By insertion of the clamping element into the hub of the cannula, the steel cannula and the core of the cable will be automatically positioned in their respective clamping slot to be tightly surrounded therein. In this manner, these two components are clamped into their desired positions at the same time, while the clamping of one component will not be affected by the other component. The clamping element is provided as a one-piece member, with its clamping slots arranged in such a configuration that the first clamping slot clamps the steel cannula when the second clamping slot clamps the core of the cable. Thus, the clamping slots have the same mutual distance as the steel cannula and the core of the cable and will be activated by displacing the clamping element.

A considerable advantage of the invention resides in the simple and safe mounting process. By displacement of the clamping member, the steel cannula and the cable are fixed relative to each other and are also fixed relative to the hub of the cannula. It is also possible to perform the clamping prior to the attaching of the steel cannula in the hub of the cannula. In this case, an adhesive is inserted into a recess of the cannula hub after insertion of the clamping element. This adhesive will enter into all gaps to thus fasten the steel cannula in the hub of the cannula. Further, the adhesive serves as a surrounding electrical shielding for the cable and lends further stability the fixation of the cable. Further, the adhesive fulfills the function to cover all metallic parts which exist on or in the hub of the cannula, thus precluding the possibility that a person might inadvertently come into contact with any one of the current-carrying parts.

According to a preferred embodiments of the invention, it is provided that the second clamping slot is formed with cutting edges adapted to penetrate an insulation of the cable. This obviates the need to first strip the cable and expose the core of the cable. When the clamping element is inserted into the hub of the cannula, the cutting of the cable insulation and the clamping of the core of the cable are performed automatically in the process.

Preferably, the clamping slots are arranged behind each other in the clamping element, with a converging opening provided between the clamping slots so as to decouple the two clamping slots from each other.

The puncture cannula of the invention is particularly suited for nerve stimulation. The instant puncture cannula is compatible with different techniques for using a cannula. Thus, for instance, an anesthetic agent can be injected directly through the steel cannula, or the steel cannula can be connected to a short catheter or a capillary tube. It is also possible to set a catheter via the puncture channel generated by the steel cannula, either with or without a guide wire.

The clamping element can be of a design adapted to various diameters of steel cannulae and/or of cores of cables.

A preferred embodiment of the invention will be described in greater detail hereunder with reference to the accompanying drawings.

DETAILED DESCRIPTION OF THE INVENTION

Figure 1:
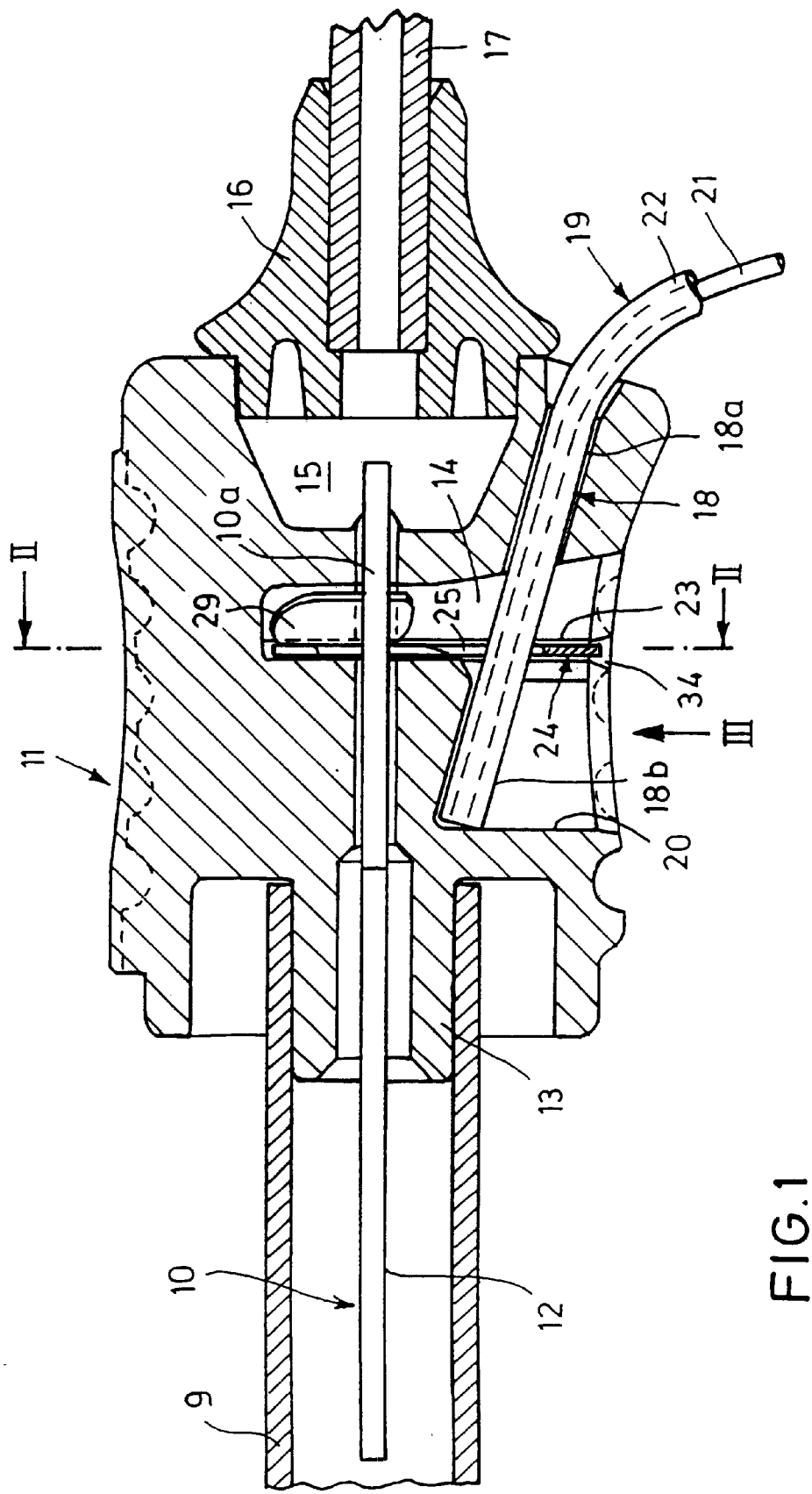
FIG. 1 is a longitudinal sectional view of an embodiment of the puncture cannula.

The puncture cannula comprises an elongate hollow steel cannula 10 attached to a cannula hub 11 of a plastic material. Steel cannula 10 consists of a tube provided with a nonconductive coating 12. The tip of the cannula 10 (not shown) is exposed.

Seated on a tubular connecting piece 13 of cannula hub 11 is a protective hose 9 which surrounds steel cannula 10 and extends beyond the length of cannula 10 to protect users from accidental injuries which might be caused by the tip of the cannula. The protective hose 9 can be withdrawn from the connecting piece 13.

The distal portion 10a extends through a cavity or a recess 14 of the hub 11 of the cannula and ends in a cavity 15 which is closed by a hose connector 16. A hose 17, starting from hose connector 16, is provided for the administration of an anesthetic agent which will then be injected into the patient's body through steel cannula 10.

Figure 2:
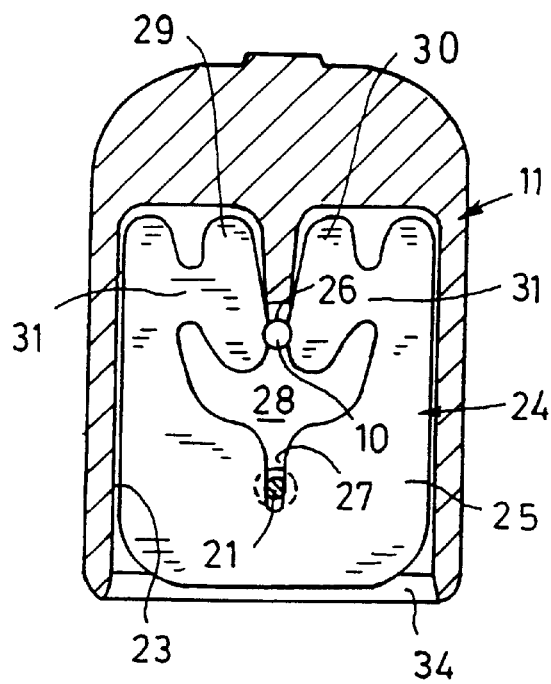
FIG. 2 is a cross-sectional view along the line II—II of FIG. 1.

An introduction channel 18 is arranged to enter the recess 14 of hub 11 and has a cable 19 extending therethrough. Introduction channel 18 is formed along a part 18a of its length as a circumferentially closed bore, while another part 18b of the length of channel 18 is formed as an open channel. The channel part 18b terminates at an end wall 20 forming a stop face for the end of cable 19. Cable 19 comprises a cable core 21 made of copper and an insulation 22. Introduction channel 18 is oriented under an acute angle relative to the longitudinal axis of steel cannula 10. A guideway 23, formed for movement of a clamping element 24 therein, is arranged in a transverse direction relative to steel cannula 10 and cable 19. Clamping element 24 comprises an elastic plate 25 made from spring steel. As illustrated in FIG. 2, this plate is formed with a first clamping slot 26 for steel cannula 10 and with a second clamping slot 27 for the core 21 of cable 19. Both clamping slots 26,27 are arranged behind each other along a common axis and have a widened opening 28 arranged therebetween. Each of the clamping slots 26,27 has a tapering shape in the direction of insertion, i.e. from top to bottom in FIG. 2, so that a progressing insertion of the clamping element 24 into the cannula hub 11 will cause an increasingly stronger clamping action on the steel cannula 10 and the cable core 21, respectively. The edges of second clamping slot 27 are cutting edges provided to cut through the insulation 22 of cable 19, thus generating a safe electrical contact to the core 21 of cable 19.

Clamping slot 26 is delimited by wings 29,30 which can be bent about bending regions 31 for adaptation to different diameters of steel cannulae 10. In FIG. 1, one of these wings, 29, is shown as bent in outward direction.

Clamping element 24 comprises a plate which, however, does not necessarily have to be flat. The plate is guided in a linear guideway 23 for displacement between a clamping position and a release position.

Figure 3:
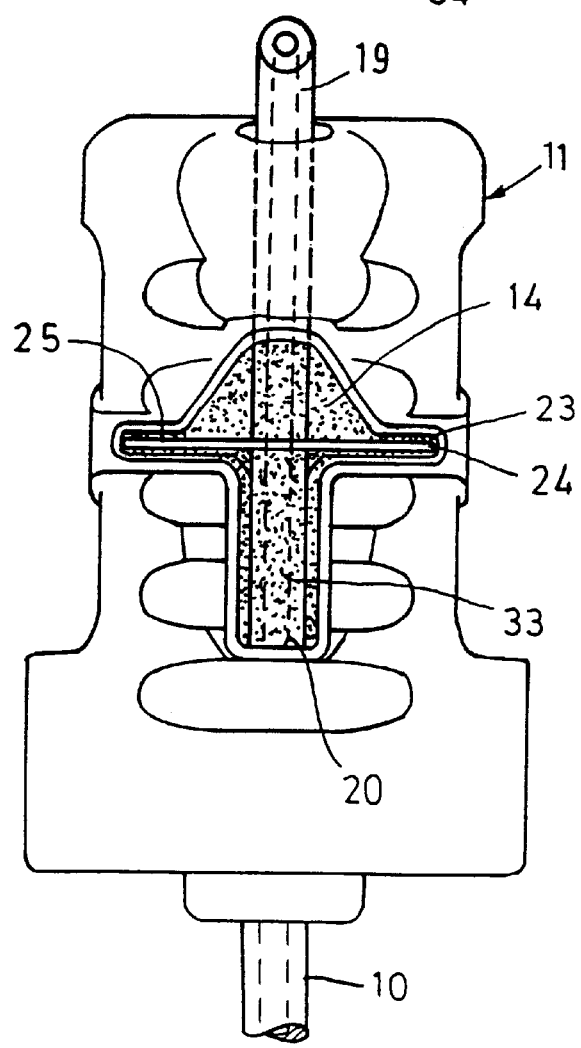
FIG. 3 is a view from the direction of the arrow III in FIG. 1.

When the steel cannula 10 and the cable 19 are to be mounted, the steel cannula 10 is inserted into the channel of cannula hub 11 which is provided for this purpose, and the cable 19 along with its insulation 22 is introduced into insertion channel 18. Subsequently, clamping element 24 is inserted into guideway 23 and pushed into the same until reaching the end stop, while the clamping slot 26 exerts a clamping grip on steel cannula 10 and the clamping slot 27 cuts through the insulation 22 into the core 21 of cable 19. The hub 11 of cannula 10 is then positioned in such an orientation that the recess 14 is facing upwards. In this condition, FIG. 3 represents a plan view from above. Next, a liquid adhesive 33 is filled into recess 14. This adhesive will occupy the recess 14 completely. The adhesive enters into the annular gap between steel cannula 10 and cannula hub 11 and into the annular gap between introduction channel 18 and the cannula hub 11 and will after hardening also keep the clamping element 24 fixed in position. Thus, a sole adhesion process is sufficient to fix all of the components relative to each other and to close them in a tightly sealed manner. Also the entrance orifice 34 of guideway 23 is closed by adhesive and sealed so that the whole clamping element 24 is embedded in adhesive material. Thus, no electrically conductive components are accessible from the outside.

What is claimed is:

1. A puncture cannula, particularly for nerve stimulation, comprising a steel cannula attached to a cannula hub and a cable extending through an insertion channel of the cannula hub and having a core connected to the steel cannula,
   wherein the hub of the cannula comprises a metallic clamping element which is formed with a first clamping slot for engaging the steel cannula and with a second clamping slot for engaging the core of the cable.

2. The puncture cannula according to claim 1, wherein the clamping element comprises a plate arranged for displacement relative to the hub of the cannula in a direction transverse to the longitudinal direction of the steel cannula, which plate is adapted to be inserted into the hub of the cannula and in the inserted condition is fixed against withdrawal.

3. The puncture cannula according to claim 1 wherein the second clamping slot has cutting edges for penetrating an insulation of the cable.

4. The puncture cannula according to claim 2, wherein the clamping slots are located behind each other in the plate and have a widened opening arranged between them.

5. The puncture cannula according to claim 1, wherein the insertion channel is at least along a part of its length formed as a bore.

6. The puncture cannula according to claim 1, wherein the hub of the cannula comprises a recess having the steel cannula and a portion of the cable passing therethrough, and wherein the recess is provided with a guideway for displacement of the clamping element.

7. The puncture cannula according to claim 6, wherein the recess is filled with adhesive.

8. The puncture cannula according to claim 7, wherein the said adhesive covers the clamping element.

9. A puncture cannula comprising a metallic needle, having a needle shaft defining an axis, extending into a cannula hub along a first bore and fixed to the cannula hub at an end opposite a needle tip; a cable comprising an electrically conductive core extending into the cannula hub along a second bore and fixed to the cannula hub; the electrically conductive core and the metallic needle being in electrical communication with one another by separately contacting a common clamping element.

10. The puncture cannula according to claim 9, wherein the clamping element comprises two slots for receiving the conductive core and the metallic needle.

11. The puncture cannula according to claim 9, wherein the clamping element comprises a slot comprising at least one cutting edge for cutting an insulation layer of the cable.

12. The puncture cannula according to claim 9, wherein the first bore and the second bore have portions that are positioned at an acute angle from one another.

13. The puncture cannula according to claim 9, wherein the cannula hub comprises a cavity recess.

14. The puncture cannula according to claim 13, wherein the cavity recess is in communication with the first bore and the second bore.

15. The puncture cannula according to claim 14, wherein the cavity recess is filled with adhesive.

16. A puncture cannula comprising:
   a cannula hub, a cannula hub first end, and a cannula hub second end;
   a needle attached to the cannula hub having a pointed tip extending away from the cannula hub first end;
   a hose for administering solutions attached to the cannula hub and extending away from the cannula hub second end;
   a cable comprising an electrically conductive core attached to a bore of the cannula hub;
   wherein the electrically conductive core of the cable is in electrical communication with the needle by separately attaching the needle and the cable to a clamping element, the clamping element comprising at least one cutting edge for cutting an insulation layer of the cable.

17. The puncture cannula according to claim 16, further comprising a cavity recess in the cannula hub.

18. The puncture cannula according to claim 17, wherein the cavity recess is filled with adhesive.

19. The puncture cannula according to claim 16, wherein the at least one cutting edge is part of a slot located on the clamping element.

20. The puncture cannula according to claim 19, where the slot is defined by a tapering opening in the clamping element.

* * * * *

UNITED STATES PATENT AND TRADEMARK OFFICE
CERTIFICATE OF CORRECTION

PATENT NO. : 6,730,083 B2
DATED : May 4, 2004
INVENTOR(S) : Freigang et al.

Page 1 of 1

It is certified that error appears in the above-identified patent and that said Letters Patent is hereby corrected as shown below:

<u>Title page,</u>
Item [30], Foreign Application Priority Data, delete "201 07 778 U", insert
-- 201 07 778.7 --.

Signed and Sealed this

Ninth Day of May, 2006

JON W. DUDAS
*Director of the United States Patent and Trademark Office*